United States Patent
Mohanraj

(10) Patent No.: US 7,537,012 B2
(45) Date of Patent: May 26, 2009

(54) MEDICAL DEVICES FOR OCCLUSION OF BLOOD FLOW

(75) Inventor: Subram Mohanraj, Fishers, IN (US)

(73) Assignee: Vasmo, Inc., Indianapolis, IN (US)

( * ) Notice: Subject to any disclaimer, the term of this patent is extended or adjusted under 35 U.S.C. 154(b) by 91 days.

(21) Appl. No.: 11/831,003

(22) Filed: Jul. 31, 2007

(65) Prior Publication Data

US 2008/0021258 A1   Jan. 24, 2008

Related U.S. Application Data

(63) Continuation of application No. 10/141,826, filed on May 10, 2002, now Pat. No. 7,249,604.

(51) Int. Cl.
*A61B 19/00*   (2006.01)

(52) U.S. Cl. .................................................. 128/899

(58) Field of Classification Search .............. 600/9–15; 128/897–899; 435/252.3, 455; 604/308, 604/891.1
See application file for complete search history.

(56) References Cited

U.S. PATENT DOCUMENTS

| | | | |
|---|---|---|---|
| 4,247,406 A | 1/1981 | Widder | |
| 4,331,654 A | 5/1982 | Morris et al. | |
| 4,345,588 A | 8/1982 | Widder et al. | |
| 4,364,377 A * | 12/1982 | Smith | 600/12 |
| 4,501,726 A | 2/1985 | Schroder | |
| 4,690,130 A | 9/1987 | Mirell | |
| 5,236,410 A | 8/1993 | Granov | |
| 5,314,679 A | 5/1994 | Lewis | |
| 5,411,730 A | 5/1995 | Kirpotin | |
| 5,427,767 A | 6/1995 | Kresse | |
| 5,753,477 A | 5/1998 | Chan | |
| 6,149,576 A | 11/2000 | Gray | |
| 6,200,547 B1 | 3/2001 | Volkonsky | |
| 6,203,487 B1 | 3/2001 | Consigny | |
| 6,364,823 B1 | 4/2002 | Garibaldi | |
| 2003/0088176 A1 | 5/2003 | Unger | |
| 2003/0215519 A1 | 11/2003 | Schwartz | |
| 2003/0219785 A1 | 11/2003 | Hallahan | |

OTHER PUBLICATIONS

Barone GW, Conerly JM, Farley PC, Flanagan TL, KRON IL, "Assessing Clamp-Related Vascular Injuries by Measurement of Associated Vascular Dysfunction", Surgery, Apr. 1989, 465-471, vol. 105.

Moore WM, Manship LL, Bunt TJ, "Differential Endothelial Injury Caused by Vascular Clamps and Vessel Loops", The American Surgeon, Jul. 1985, 392-400, vol. 5.

Margovsky AI, Lord RSA, Chambers AJ, Aust. N.Z. J., "The Effect of Arterial Clamp Duration On Endothelial Injury: An Experimental Study," Surgery, 1997, 448-451, vol. 67.

(Continued)

*Primary Examiner*—Samuel G Gilbert

(57) ABSTRACT

A medical, surgical, or operating kit for occluding or controlling blood flow or fluid flow is disclosed. The kit is comprised of (a) a dispersion of magnetic microparticles which can be administered into a blood vessel or fluid vessel, and (b) an external magnetic field source which is adapted to be placed at the desired site above the path of the bloodstream or fluid flow to form a plug or blockade within the blood vessel or fluid vessel that occludes or controls blood flow or fluid flow.

31 Claims, 4 Drawing Sheets

OTHER PUBLICATIONS

Jackiewicz TA, McGeachie JK, Tennant M, "Structural Recovery of Small Arteries Following Clamp Injury: A Light and Electron Microscopic Investigation in the Rat," Microsurgery, 1996, 674-680, vol. 17.

Litchford B., Okies JE, Sugimura S, Starr A., J. Thorac., "Acute Aortic Dissection From Cross-Clamp Injury", Cardiovasc. Surg., 1976, 709-713, vol. 72.

Archie JP Jr., "Early Postoperative Femoral-Distal Bypass Graft Failure Due to Vascular Clamp Injury Induced Common Femoral Artery Thrombosis", The American Surgeon, 1988, 167-168, vol. 54.

Manship LL., Moore WM., Bynoe R., Bunt TJ, "Differential Endothelial Injury Caused by Vascular Clamps and Vessel Loops II", The American Surgeon, 1985, 401-406, vol. 5.

Bellamy RF., "The Causes of Death in Conventional Land Warfare: Implications for Combat Casualty Care Research", Military Medicine, 1984, 55-62, vol. 149.

Sauaia A et al., J., "Epidemiology of Trauma Deaths: A Reassessment", Trauma, Feb. 1995, 185-193, vol. 38.

Fraser, MO, "The Future of Bladder Control—Intravesical Drug Delivery, a Pinch of Pepper, and Gene Therapy", Reviews in Urology, 2002, vol. 4, 1-11.

\* cited by examiner

MEDICAL DEVICES FOR OCCLUSION OF BLOOD FLOW

This application is a continuation of application Ser. No. 10/141,826, filed on May 10, 2002, now Pat. No. 7,249,604.

BACKGROUND OF THE INVENTION

Vascular blood flow is now most commonly occluded during surgery by either clamping or ligation. Blood vessels are lined internally with a single layer of endothelial cells which are joined laterally by tight junctions and which overlie a layer of smooth muscle cells. This endothelial lining forms a permeability barrier to prevent the passage of large molecules between the blood and the extra corporeal space. Clamping or ligation results in trauma to the vessel and disruption of the endothelial cell permeability barrier (Barone GW, Conerly JM, Farley PC, Flanagan TL, Kron IL, Surgery 105:465-471, 1989; Moore WM, Manship LL, Bunt TJ, Am. Surg. 5:392-400, 1985; Margovsky AI, Lord RSA, Chambers AJ, Aust. N. Z. J. Surg. 67:448-451, 1997). In one study, these effects persisted for at least two weeks after a clamping period of only five minutes (Jackiewicz TA, McGeachie JK, Tennant M, Microsurg. 17:674-680, 1996). Compromising the permeability barrier allows the passage of factors in the blood which promote smooth muscle cell growth such as the platelet-derived growth factor (Jackiewicz TA, McGeachie JK, Tennant M, Microsurg. 17:674-680, 1996). Clamp injury can therefore cause later formation of atherosclerotic plaque and stenosis at the clamp site (Margovsky AI, Lord RSA, Chambers AJ, Aust. N. Z. J. Surg. 67:448-451, 1997). In addition, clamping can cause immediate peri-operative complications such as arterial dissection (Litchford B, Okies JE, Sugimura S, Starr A, J. Thorac. Cardiovasc. Surg. 72:709-713, 1976) or thrombosis due to embolization of atherosclerotic plaque to distal portions of the circulation (Archie JP Jr, Am. Surg. 54:167-168, 1988). Diseased vessels, such as those encountered during coronary artery revascularization, are especially prone to both immediate and long-term deleterious effects of clamping or ligation (Manship LL, Moore WM, Bynoe R, Bunt TJ, Am. Surg. 5:401-406, 1985). Noncompressible hemorrhage continues to be a primary cause of death in both military and civilian trauma (Bellamy R F. Mil. Med. 149:55-62, 1984; Sauaia A et al J. Trauma 38:185-193, 1995). Currently there is no treatment short of surgery for severe abdominal bleeding resulting from either blunt or penetrating injury. Vascular injuries in the region of the groin continue to be largely untreatable.

The use of magnetic particles for different applications in medicine has been reported for a long time. The most representative examples follow. U.S. Pat. No. 4,247,406 (Widder et al, 1981), U.S. Pat. No. 4,345,588 (Widder et al, 1982), U.S. Pat. No. 4,331,654 (Morris et al, 1982), U.S. Pat. No. 4,501,726 (Schroder et al, 1985), U.S. Pat. No. 4,690,130 (Mirell SG, 1987), U.S. Pat. No. 5,411,730 (Kirpotin et al, 1995),U.S. Pat. No. 5,427,767 (Kresse et al, 1995),U.S. Pat. No. 5,753,477 (Chan, 1998), and U.S. pat. application Ser. No. 0219785 A 1 (Hallahan et al., 2003) disclose the use of magnetic carriers for localized delivery of therapeutic or diagnostic agents. U.S. Pat. No. 5,314,679 (Lewis et al, 1994) and U.S. patent application Ser. No. 09/852,421 (Unger, 2003) disclose the use of magnetic particles as contrast agents for magnetic resonance imaging. U.S. patent application Ser. No. 10/389,708 (Schwartz et al, 2003) discloses a method to embolize a vascular site using a microparticle comprised of a hydrolyzable crosslinked hydrogel. In this patent application, magnetic particles are also included as contrast agents in the hydrogel for magnetic resonance imaging. The mechanism of embolization here is the hydrolyzation of the crosslinked hydrogel. U.S. Pat. No. 6,303,487 B1 (Consigny PM, 2001) discloses the use of magnetic particles in the focal delivery of cells.

U.S. Pat. No. 6,364,823 B1 (Garibaldi et al, 2002) discloses the use of magnetic particles for controlling the delivery of an embolic agent to a vascular defect. The purpose of Garibaldi's work is the delivery of embolic materials to the site of the vascular defect using magnetic means. A liquid embolic agent is provided with a magnetic constituent to be drawn into the defect using an applied magnetic field. The embolic agent, after reaching the vascular defect, precipitates a polymer which in combination with a glue, seals the vascular defect. In essence, the purpose of the magnetic material is to deliver the embolic agent with the precipitating polymer and glue to the site of the vascular defect. This application is similar to the targeted delivery of pharmaceutical agents to a particular site except that the agent here is an embolic material. Basically, in the above applications, magnetic particles have been used as a carrier to take a pharmaceutical or embolic agent to a particular location.

U.S. Pat. No. 5,236,410 (Granov et al, 1993) discloses a method of treatment for a tumor using a magnetically hard, radio-opaque, ferromagnetic material suspended in an oil solution of an oil-soluble anti-tumor substance. A suspension of demagnetized ferromagnetic particles in an oil solution of an anti-tumor substance is drawn into the area of the tumor using an applied magnetic field. The ferromagnetic particles become remagnetized and, because of the high residual magnetism of the hard ferromagnetic material, form a porous body of aggregates at the tumor area. One purpose of the oil-suspended hard ferromagnetic material is to deliver as a carrier the oil-soluble anti-tumor substance to the tumor area and another purpose is to retain it within the tumor area by embolization of the hard ferromagnetic material. The major purpose of the oil-suspended hard ferromagnetic material, however, is for its use in hyperthermia. The distinction of Granov's method, compared to other hyperthermia methods or chemotherapy, is that Granov utilizes both chemotherapy and hyperthermia in trying to produce necrosis of the tumor tissue. U.S. Pat. No. 6,149,576 (Gray et al, 2000) discloses the use of a ferromagnetic material to treat a tumor tissue by producing hyperthermia with the application of a rotational magnetic field.

U.S. Pat. No. 4,364,377 (Smith F W, 1982) discloses a method to repair or fix a lesion in the gastrointestinal tract. Under his method a ferromagnetic tamponading mass is introduced into the gastrointestinal tract near a bleeding lesion by the use of a catheter. The tamponading mass forms near the lesion due to the high residual magnetism of the ferromagnetic particles. An external magnetic field generator is used to move the tamponading mass and position it to close the lesion hole. The tamponading mass stops the bleeding once it has been positioned at the lesion. In Smith's method the ferromagnetic tamponading mass is introduced into the gastrointestinal tract and the tamponading mass is formed without the use of the external magnetic field. The main purpose of the external magnetic field generator is to move the tamponading mass to the position of the lesion.

The present invention relates to the occlusion of blood vessels to stop the flow of blood, especially during elective or emergency surgical procedures or following traumatic injury.

The invention is a safer alternative vascular occlusion method which has none of the injurious effects of clamping or ligation described above.

SUMMARY OF THE INVENTION

The present invention discloses a method for the occlusion of blood vessels or fluid vessels to stop the flow of blood or fluid during elective or emergency surgical procedures or following traumatic injury. The present invention also discloses a medical device or tool for occluding, reducing, or controlling blood flow or fluid flow. In this invention, a plug or blockade is formed to occlude, reduce, or control blood flow or fluid flow when magnetic microparticles, nanoparticles, or colloids are administered into a blood vessel or fluid vessel, and an external magnetic field source is placed or held at the desired site near or above the path of the blood stream or fluid flow. The device can occlude blood flow or fluid flow in a reversible or non-reversible manner for a variety of surgical, medical, and other applications.

DETAILED DESCRIPTION OF THE INVENTION

The present invention discloses a method for the occlusion of blood vessels or fluid vessels to stop the flow of blood or fluid during elective or emergency surgical procedures or following traumatic injury. The present invention also encompasses a medical device, clinical tool, research tool, or operating tool for occluding, reducing, or controlling blood flow or fluid flow. The method for occluding, reducing, or controlling blood flow or fluid flow is comprised of the following steps:

(a) magnetic microparticles, magnetic nanoparticles, or magnetic colloids are administered in the form of a dispersion or suspension into a blood vessel, fluid vessel, tube or pipe, and (b) an external magnetic field source is placed or held at the desired site near or above the path of the blood stream or fluid flow, and (c) a plug or blockade that occludes, reduces, or controls blood flow or fluid flow is formed as a result.

The medical device, clinical tool, or operating tool for occluding, reducing, or controlling blood flow or fluid flow is comprised of:

(a) magnetic microparticles, magnetic nanoparticles, or magnetic colloids which are administered in the form of a dispersion or suspension into a blood vessel, fluid vessel, tube or pipe, and (b) an external magnetic field source which is placed or held at the desired site near or above the path of the blood stream or fluid flow, and (c) a plug or blockade, which is formed as a result, that occludes, reduces, or controls blood flow or fluid flow.

The medical device, clinical tool, or operating tool which also encompasses the method for occluding, reducing, or controlling blood flow or fluid flow are hereinafter grouped under the term "Magnetic Medical Device" or "MMD". The magnetic microparticles, magnetic nanoparticles, and/or magnetic colloids are hereinafter grouped under the term "magnetic microparticles". The external magnetic field source to be placed or held at the desired site near or above the path of the blood stream or fluid flow is hereinafter referred to as "external magnetic field source" or "EMFS".

The present invention is a safer alternative vascular occlusion method which has none of the injurious effects of clamping or ligation. This is because the magnetic microparticles in the occluding plug exert very little pressure or shear force on the endothelial cell lining. This novel technology is intended for the occlusion of blood vessels to stop the flow of blood during elective or emergency surgical procedures or following traumatic injury. Another intended use of this technology is for the occlusion of blood vessels to control internal hemorrhage. This new invention will offer the surgeon or paramedic a means of occluding blood vessels while causing little or no injury to the vessel itself, as compared with current methods of clamping or tying to occlude blood flow, which damage both the endothelial cells lining the vessel as well as the smooth muscle cells in the vessel wall.

The MMD for occluding, reducing, or controlling blood flow or fluid flow in this invention is quite flexible. It can be used for any application involving occlusion, reduction, or control of blood flow or fluid flow. The invention can be adapted for a wide range of surgical and medical procedures. The MMD can be adapted to control and manage incontinence. The potential applications can be extended to virtually every aspect of the surgical and trauma treatment fields.

In this invention, a plug or blockade is formed to occlude, reduce, or control blood flow or fluid flow when magnetic microparticles are administered into a blood vessel or fluid vessel, and an external magnetic field source is placed or held at the desired site near or above the path of the blood stream or fluid flow. The EMFS can be placed or held at the desired site near or above the path of the blood stream or fluid flow either before, during, or after the infusion of the magnetic microparticles into the blood vessel or fluid vessel. An EMFS, such as a powerful NdFeB magnet no larger than an inch in diameter and weighing no more than five grams, can be placed near or above the vessel to be occluded for no more than the time required to maintain the blockade/occlusion. The design and utilization of this technology are demonstrated in Examples and FIGS. 1-13. It is important to point out that the magnetic microparticle preparations tested in vivo were indeed able to form a plug, under physiological flow conditions, in all three artery types tested (carotid, femoral, and coronary; see Examples and FIGS. 1-9). This phenomenon is rapid and completely reversible. The effects of plug formation can be either non-reversible or reversible. After the purpose of the occlusion is complete, the EMFS can be removed to dissolve or redisperse the microparticle plug or blockade resulting in the resumption of blood flow. This is shown in Examples and FIGS. 4-6. Therefore, after the required occlusion, there is no need for surgical removal because the microparticles redisperse into a colloidal form. The magnetic microparticles are also biodegradable and non-toxic. The required external magnetic field source can be placed or held either internal or external to the body, even though the external magnetic field source is external to the particular blood vessel or other vessel of interest. Non-invasive, minimally invasive, or invasive procedures can be utilized with the MMDs.

It has been shown in the inventor's laboratory that colloidal dispersions of magnetic microparticles, under flow conditions, display rapid formation of a plug in the presence of an external magnetic field. As soon as the external magnetic field source is removed, the redispersion or dissolution of the plug occurs, allowing the resumption of flow inside the blocked vessel. The plug formation of microparticle dispersions in the presence of an external magnetic field was also observed with ferrimagnetic and ferromagnetic microparticles.

In vitro plug formation was observed to occur as soon as the particles were injected with the EMFS in place. In other words, the moment the particles passed under the EMFS, a plug was formed to block flow. Plug formation in vivo was also rapid. The limitation on determining how rapid was due to the time required to inject contrast media and take the x-ray. Thus, blockage occurred within 30 seconds to 2 minutes.

Concerning plug dispersal, in vitro experiments indicated that this occurred rapidly, i.e., within 30 to 90 seconds. Complete plug dispersal in vivo was slower than in vitro, taking between three and eight minutes in the femoral artery (FIG. 5).

Magnetic microparticles with a range of diameters, surface properties, magnetic properties, and microencapsulating materials were used in the inventor's laboratory for the occlusion of blood flow or fluid flow. The plug formation of the microparticle dispersion in the presence of an EMFS, and the redispersion of the microparticles after the removal of the external magnetic field depend on particle size and size distribution, surface characteristics, magnetic properties, and matrix properties.

In order to occlude specific blood vessels, sizes were chosen from a range with an upper limit dictated by the diameter of the venules, vessels, or capillaries and a lower limit set by the ability to form a useful plug. One would not want the size to be so big that there is occlusion in the absence of an EMFS. The sizes of the magnetic microparticles ranges from 0.01 to 2000 micrometers, preferably 0.01 to 200 micrometers, and optimally 0.02 to 50 micrometers.

The magnetic microparticles are comprised of any magnetizable materials such as paramagnetic, superparamagnetic, ferrimagnetic, or ferromagnetic materials. The magnetic microparticles are alternatively comprised of one or a plurality of plain magnetic materials, surface-modified materials, coated microparticles, coated nanoparticles, microencapsulated microparticles, microencapsulated nanoparticles, microencapsulated microspheres, microencapsulated colloidal systems, microencapsulated liposomes and emulsions, or embedded systems comprised of magnetic ingredients.

The magnetic microparticles are alternatively comprised of or treated with emulsifiers, surfactants, lipids, polymers, copolymers, silicones, silanes, or other agents which modify the surface or encapsulate. The magnetic microparticles are alternatively comprised of one or a plurality of therapeutic drugs, pharmaceutical compounds, hemostatic agents, or other bioactive agents to enhance the performance of the therapy or treatment.

The external magnetic field source is comprised of, but not limited to: (a) rare earth magnets including, but not limited to, Neodymium Iron Boron magnets, bonded Neodymium Iron Boron magnets, and Samarium Cobalt magnets, or (b) ceramic magnets, or (c) ceramic ferrite magnets, or (d) Alnico magnets, or (e) any other permanent magnets. The external magnetic field source is alternatively comprised of electromagnets, superconducting magnets, or any other magnetic field generators.

EMFS no larger than an inch in diameter, weighing no more than five grams, and comprised of powerful Neodymium-Iron-Boron (NdFeB) magnets, were used in the animal studies. With energy products ranging from 26 to 48 MGOe, NdFeB is the preferred choice for these high performance applications. The EMFS can be tailor-made to the size and shape (contoured to the needs of the surgeon) and required attraction for clinical studies. This treatment will be easy to reduce to practice in the clinical setting with a NdFeB magnet of the size of a quarter (one inch diameter) and weighing about five grams.

EXAMPLES

Magnetic microparticles with various diameters and magnetic properties were developed, tested and evaluated in animal models for their efficiency to occlude blood flow in various vessels.

a) Fine dispersions of magnetizable materials such as magnetite were prepared using procedures well-established at the inventors facility and briefly described as follows: Fine dispersions of magnetite were prepared by dissolving divalent Fe ions and trivalent Fe ions in an aqueous solution and adding an alkali metal hydroxide to the solution with thorough mixing to form fine particles of magnetite. The diameters of the above magnetic microparticles ranged from 0.01 to 50 micrometers. These microparticles are super paramagnetic and their attraction time on a small 1 inch×2 inch ceramic magnet is 1-2 seconds. These magnetic particles are highly hydrophilic. Magnetic susceptibilities of these magnetic microparticles are 30000-40000 cgs/g.

b) Surface modified magnetic microparticles were prepared by treating the above magnetizable materials with emulsifiers, surfactants, lipids, or other reagents. The following surface-active materials were used: long-chain carboxylates, alkyl sulfonates, oxyethylenated nonyl phenols, polyvinyl alcohols, polyethylene glycol, and silanes. Surface-modified particles include charged surface groups or moieties for better or longer circulation in the blood, thereby allowing them to recirculate and to be trapped at the desired site using an external magnetic field. The diameters of the above magnetic microparticles ranged from 0.01 to 100 micrometers. These microparticles are super paramagnetic and their attraction time on a small 1 inch×2 inch ceramic magnet is 1-2 seconds. Magnetic susceptibilities of these magnetic microparticles are 30000-40000 cgs/g.

c) Polymer coated or encapsulated magnetic microparticles were prepared using the above magnetizable materials and polymer materials such as polylactides and copolymers of lactide and glycolide. These microparticles are super paramagnetic and their attraction time on a small 1 inch×2 inch ceramic magnet is 1-3 seconds. Magnetic susceptibilities of these magnetic microparticles are 30000-50000 cgs/g. The diameters of the above magnetic microparticles ranged from 0.01 to 200 micrometers.

The external magnetic field sources suited for these applications include Neodymium-Iron-Boron (NdFeB) magnets. In these experiments, NdFeB disc magnets were used.

In Vivo Studies on MMDs for Occlusion of Blood Flow

The MMDs have been tested and evaluated in animal models for their efficiency to occlude blood flow in various vessels. Animal studies have been performed to show the technology for in vivo use. Examples of experiments conducted are shown below:

Using juvenile farm pigs as an experimental model, the MMDs have been tested for their efficiency to occlude blood flow in various vessels. It has been shown that the new MMDs can occlude the blood flow in carotid, femoral, and coronary arteries.

Experimental Protocol: Juvenile farm pigs weighing 50 to 60 kg were used in this study. The animals were divided into 3 groups: carotid artery, femoral artery, and coronary artery. All animals received a normal diet. Animals underwent either femoral or carotid artery cut down. An 8F sheath was inserted into the artery. After systemic heparinization, an 8F guiding catheter was used to engage carotid, femoral, or coronary arteries. After a baseline arterial angiogram was performed, the EMFS was placed over the target artery. Contrast material was injected to insure that the target vessel was not in spasm and the EMFS was positioned over the target vessel. As soon as the position of the EMFS was optimized, the dispersed magnetic microparticles were infused at a rate of 1 ml/min. Angiography was performed repeatedly 30-60 seconds after the infusion of microparticles to assess arterial flow.

Results: Local delivery of the microspheres was well-tolerated by all animals. No hemodynamic, heart rate, or blood pressure changes were noted. Successful occlusion of blood flow by the medical device was achieved in carotid, femoral, and coronary artery beds.

An example of such successful occlusion of blood flow with the MMD in the carotid artery is shown in FIGS. 1-3. FIG. 1 is the baseline angiogram of a farm pig's right carotid artery (1) with the arrow showing the direction of the blood flow. FIG. 2 is an angiogram with an external magnetic field source (2) placed on the skin above the pig's right carotid artery; continuous blood flow is evident on either side of the external magnetic field source (2) in the carotid artery (1A) and (1B). FIG. 3 is an angiogram showing the pig's occluded right carotid artery one minute after microparticle infusion. Blood flow in the carotid artery (1A) is stopped right at the point below the external magnetic field source (2) and no blood flow is seen in the carotid artery (1B) beyond the external magnetic field source (2), which indicates a complete occlusion of the right carotid artery.

An example of a successful occlusion of blood flow with the MMD in the femoral artery is shown in FIGS. 4-6. FIG. 4 is an angiogram showing "no blood flow" in the superficial femoral artery (3) of a farm pig less than one minute after microparticle infusion with an external magnetic field source (4) placed on the skin above the pig's superficial femoral artery (3). Thus selective total occlusion of the superficial femoral artery (3) is achieved. FIG. 5 is an angiogram showing a partial resumption of blood flow in the superficial femoral artery (3) three minutes after removal of the external magnetic field source. FIG. 6 is an angiogram showing a complete resumption of the blood flow in the superficial femoral artery (3) eight minutes after removal of the external magnetic field source. The phenomenon is therefore completely reversible.

An example of a successful occlusion of blood flow with the MMD in the coronary artery is shown in FIGS. 7-9. FIG. 7 is a baseline angiogram of the left anterior descending coronary artery (7) of a farm pig. In FIGS. 7-9, the guiding catheter (C) is used to engage the coronary arteries. FIG. 8 is an angiogram of the left anterior descending coronary artery (7) with the external magnetic field source (8) placed on the ribs. FIG. 9 is an angiogram showing "no blood flow" in the left anterior descending coronary artery (7) two minutes after infusion of the microparticle dispersion. A complete occlusion of the left anterior descending coronary artery is achieved.

Occlusion was rapid in all cases. The target artery resumed blood flow after removal of the EMFS within minutes. This is shown in the example with the femoral artery in FIGS. 4-6. These results clearly demonstrate the usability of the magnetic microparticles in conjunction with the EMFS as a MMD to block blood flow reversibly in vivo. The MMD can be adapted to any branches of the arteries. FIGS. 10-13 show the subselection of coronary branches and the respective placement of the EMFS for the desired site of occlusion. FIG. 10 is a baseline angiogram of the left coronary artery of a farm pig. FIG. 11 is an angiogram of the left coronary artery with the external magnetic field source (10) placed selectively above the rumus branch (9) on the ribs. FIG. 12 is another baseline angiogram of the left coronary artery of a farm pig. FIG. 13 is an angiogram of the left coronary artery with the external magnetic field source (12) placed selectively above the diagonal branch (11) on the ribs. The coronary branches shown can be selectively occluded for various applications.

Safe and effective reversible occlusion of vascular blood flow has been demonstrated in animals under surgical conditions. A range of products in kit form could be used in a variety of surgical and trauma applications.

MMD as a Non-Invasive Tool for use in Neuroscience:

The MMD can be used as a non-invasive method of focal stroke/ischemia induction in experimental animals. It has been shown that injection of magnetic microparticles into the circulatory system in conjunction with focal placement of EMFS results in the formation of consistent focal ischemic lesions within the brain. This novel experimental tool will facilitate neuroscience research particularly into the mechanisms underlying stroke and ischemia and at the same time provide a method for routine evaluation of pharmacological compounds with the potential to reduce the debilitating effects of stroke in humans.

Experimental Protocol: A series of animals were tested for the ability of the MMD to induce ischemic lesions. A dispersion of magnetic microparticles was slowly delivered to each animal via tail vein injection with no apparent physiological stress. Breathing rate appeared to be normal during the injection protocol. At the start of the tail vein injection an EMFS was placed in the temporal region of the brain. At the end of the injection session each animal was carefully monitored for any adverse signs. None were noted. These animals were then monitored frequently over the next 4 days and were found to be eating normally and also had normal behavioral patterns. At the end of 4 days each animal was sacrificed. The external surface of the brain showed no overt signs of injury (cortical signs of lesions on the surface). The internal organs did not reveal any visual deposition of the magnetic microparticles.

Results: Considerable histopathology was found in the hippocampus (CA1, CA3) and within the hilus of the dentate gyrus (DG). The pyramidal cell layer was nearly obliterated indicating that the blood flow to this brain region (middle cerebral artery) had been blocked for some time. Virtually all of the hilar neurons were also missing in these animals. These results were attributed primarily to reduced blood flow to this region that resulted in large scale ischemia and subsequent neuronal death.

These results demonstrate the feasibility of the use of this new technology as a tool in neuroscience.

Applications of MMD

The new MMDs offer the surgeon or paramedic a means of occluding blood vessels while causing little or no injury to the vessel itself, as compared with current methods of clamping or tying to occlude blood flow, which damage both the endothelial cells lining the vessel as well as the smooth muscle cells in the vessel wall. This is because the magnetic microparticles in the occluding plug exert very little pressure or shear force on the endothelial cell lining. An EMFS can be placed at the desired site of occlusion near or above the vessel to be occluded for no more than the time required to maintain the blockade/occlusion. The MMD can be used during surgery to arrest blood flow in a reversible manner without the use of clamps or ligatures. The MMD could be used for the occlusion of blood vessels to stop the flow of blood during elective or emergency surgical procedures or following traumatic injury. The MMD could be adapted for a wide range of surgical and other medical procedures, including, but not limited to cardiac bypass surgery, vascular surgery, renal transplantation, incontinence therapy, hemorrhage control, EMT trauma, and battlefield trauma.

Examples of Applications

This new technology could be utilized during surgical or medical procedures involving the coronary artery. FIGS. 7-13 show the usability of the MMD on the coronary artery of a farm pig. FIG. 8 shows the baseline angiogram of the left anterior descending coronary artery with the external magnetic field source placed on the ribs. FIG. 9 shows a complete occlusion of the left anterior descending coronary artery two minutes after infusion of the magnetic microparticle dispersion.

1. Coronary artery bypass grafting (CABG): The use of the MMD to occlude the left anterior descending coronary artery (LAD) during bypass grafting would avoid any compression of the coronary artery during the procedure, and spare the endothelial cell lining from injury. This should improve the long-term surgical outcome by minimizing atherosclerotic changes in the occluded region of the vessel.

2. Surgical correction of deep vein thrombosis (DVT): The use of the MMD to occlude blood flow in the affected vein in lieu of clamping or tying would avoid damaging the vein in that region and prevent the introduction of a possible new attachment site for post surgical thrombus formation.

3. For controlling hemorrhage: The MMD is capable of controlling hemorrhage from vascular injuries in the proximal extremities. The device will be especially useful for the treatment of injuries that are not amenable to tourniquet application. Vascular injuries in the region of the groin continue to be largely untreatable. The MMD technology can easily be used to control hemorrhage in the groin. The usability of the device for this application is shown in the example with the femoral artery of a farm pig (FIGS. 4-6). FIG. 4 shows selective total occlusion of one of the superficial femoral arteries less than one minute after microparticle infusion. This process can also be reversible, in that after the necessary procedure, blood flow can be resumed. FIG. 6 shows complete resumption of the blood flow eight minutes after removal of the external magnetic field source.

The MMD could also be used to control noncompressible hemorrhage. Noncompressible hemorrhage continues to be a primary cause of death in both military and civilian trauma (Bellamy R F, Mil. Med. 149:55-62, 1984; Sauaia A et al, J. Trauma 38:185-193, 1995). Currently there is no treatment short of surgery for severe abdominal bleeding resulting from either blunt or penetrating injury. Utilization of the new device, that is by infusion of magnetic microparticles through a trocar and holding the external magnetic field source above the site, will stop the bleeding. A hemostatic agent could be included in the magnetic microparticle dispersion to promote coagulation and provide hemostasis. The MMD can also control severe intracavitary hemorrhage. The MMD can limit the immediate, short- and long-term deleterious consequences of severe hemorrhage. This procedure can be noninvasive, minimally invasive, or invasive.

4. As a tool for use in Neuroscience: The MMD can be used as a non-invasive method of focal stroke/ischemia induction in experimental animals. This novel technology will facilitate neuroscience research particularly into the mechanisms underlying stroke and ischemia and at the same time provide a method for routine evaluation of pharmacological compounds with the potential to reduce the debilitating effects of stroke in humans.

5. For controlling incontinence: The MMD can be adapted to control or manage incontinence. The incidence of urinary incontinence and overactive bladder problems will continue to grow as the population ages (Fraser M O et al, Reviews in Urology, 4: 1-11, 2002). New technology is essential for improved treatment of an estimated 17 million men and women with bladder control problems. The MMD could be adapted for effective treatment of incontinence problems. Anticholinergic agents could be included with magnetic microparticles for improved therapy.

6. Other Applications

The examples outlined above as possible applications for the occlusion of blood flow by the use of the MMD are intended only to be suggestive of the many possible uses of the MMD in surgical and other fields. The area of trauma surgery, including battlefield trauma, and the use of the MMD by paramedics to stop hemorrhage, are two other medical applications that could prove effective.

Future products could include surgical kits to be used in cardiac bypass surgery, vascular surgery, renal transplant surgery, EMT trauma, and battlefield trauma. Future products could include kits for embolization. In addition, future products could include site-specific drug delivery.

BRIEF DESCRIPTION OF THE DRAWINGS

FIG. 1: A baseline angiogram of a pig's right carotid artery.

FIG. 2: An angiogram with an external magnetic field source placed on the skin above the pig's right carotid artery.

FIG. 3: An angiogram of the pig's occluded right carotid artery after microparticle infusion.

FIG. 4: Selective total occlusion of one of the superficial femoral arteries of a farm pig is shown after less than one minute of microparticle infusion.

FIG. 5: Partial resumption of blood flow is shown after three minutes of removal of the external magnetic field source.

FIG. 6: Complete resumption of the blood flow is shown after eight minutes of removal of the external magnetic field source.

FIG. 7: A baseline angiogram of the left anterior descending coronary artery of a farm pig.

FIG. 8: An angiogram of the left anterior descending coronary artery with the external magnetic field source placed on the ribs.

FIG. 9: Complete occlusion of the left anterior descending coronary artery is shown after two minutes of infusion of the microparticle dispersion.

FIG. 10: A baseline angiogram of the left coronary artery.

FIG. 11: An angiogram of the left coronary artery with the EMFS placed selectively above the rumus branch on the ribs.

FIG. 12: Another baseline angiogram of the left coronary artery.

FIG. 13: An angiogram of the left coronary artery with the EMFS placed selectively above the diagonal branch on the ribs.

Figure 1:
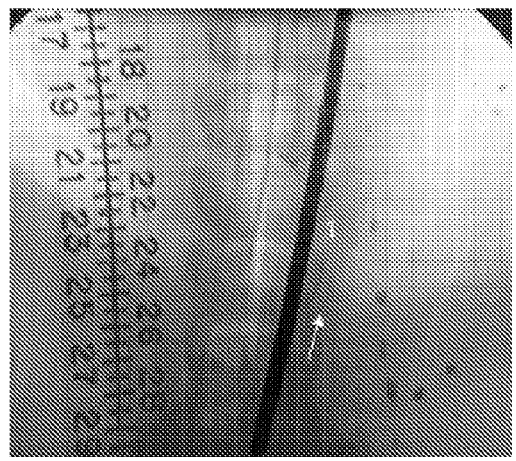
FIGS. 1-3: Evaluation of MMD on the right carotid artery of a farm pig.
Figure 2:
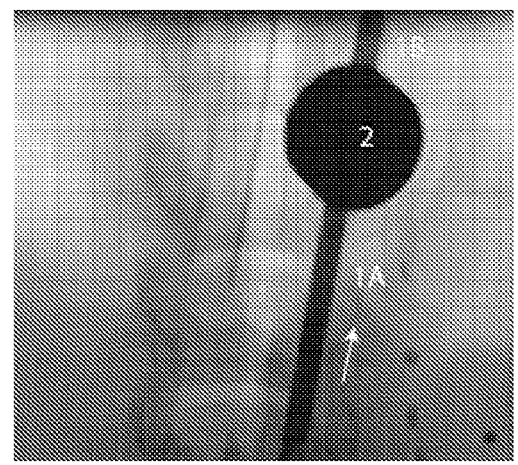
Figure 3:
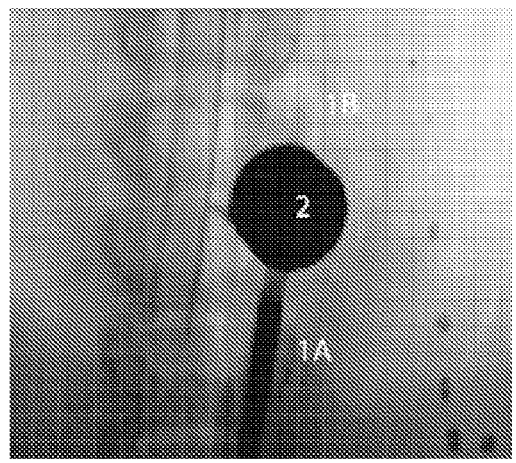
Figure 4:
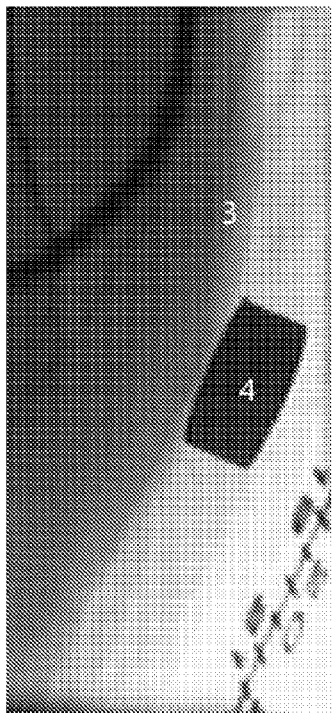
FIGS. 4-6: Evaluation of MMD on the superficial femoral artery of a farm pig.
Figure 5:
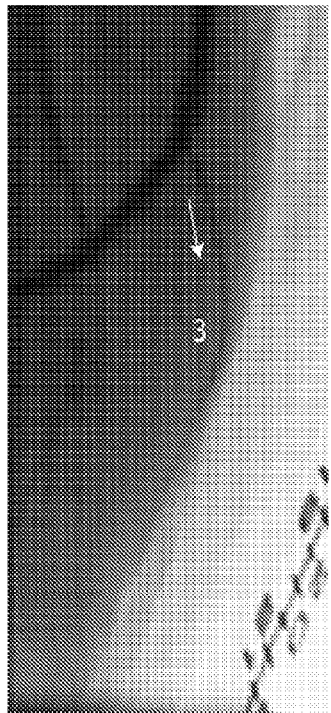
Figure 6:
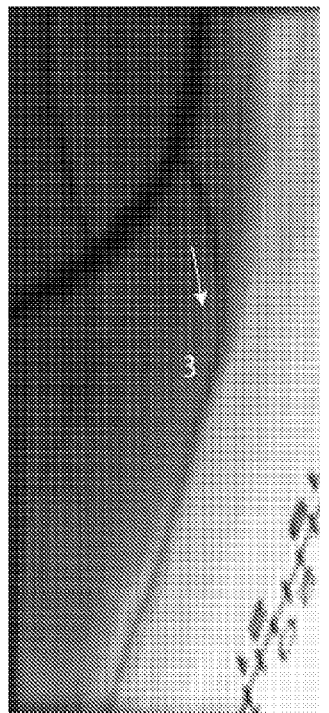
Figure 7:
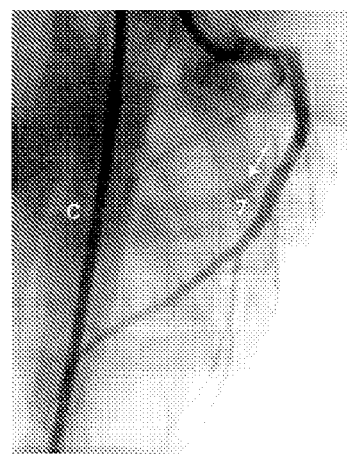
FIGS. 7-9: Evaluation of MMD on the coronary artery of a farm pig.
Figure 8:
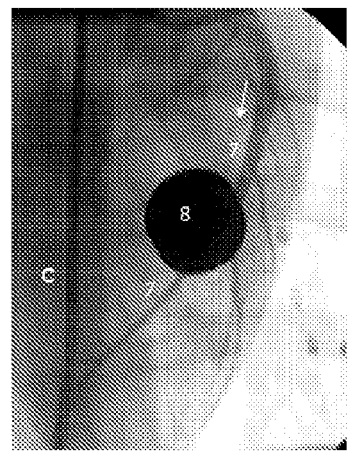
Figure 9:
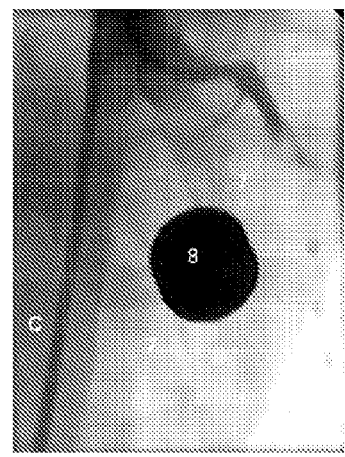
Figure 10:
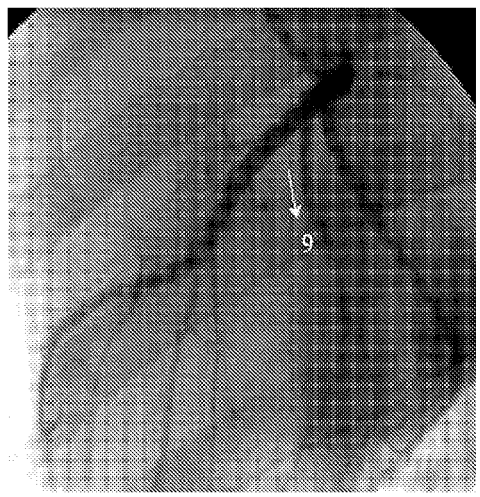
FIGS. 10-13: Subselection of coronary branches of farm pigs and the respective placement of the EMFS for the desired site of occlusion.
Figure 11:
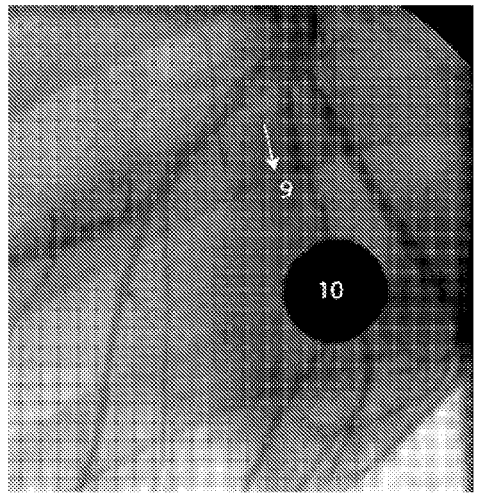
Figure 12:
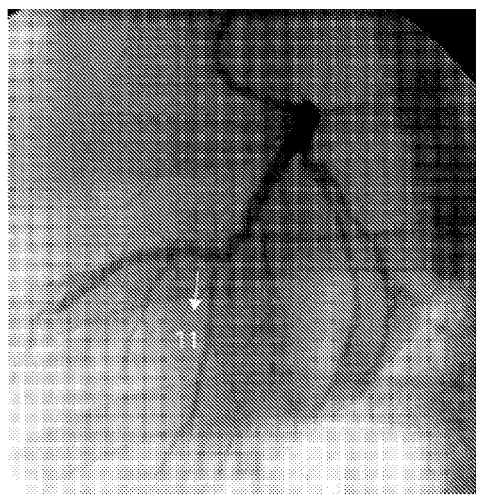
Figure 13:
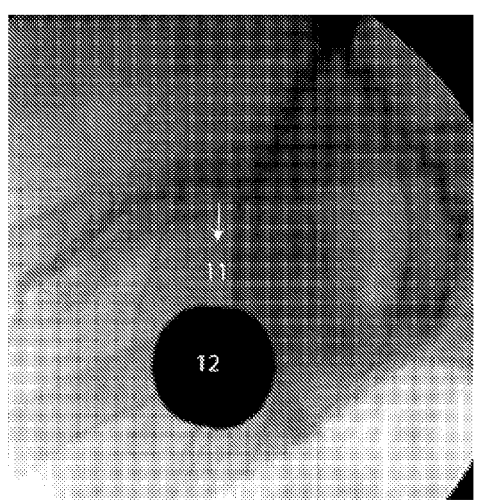

What is claimed is:

1. A medical, surgical, or operating kit for occluding or controlling blood flow comprised of:

(a) magnetic microparticles, magnetic nanoparticles, or magnetic colloids which can be administered in the form of a dispersion or suspension into a blood vessel that flows through the vessel in the bloodstream, and (b) an external magnetic field source which is adapted to be placed or held at the desired site near or above the path of the bloodstream to form a plug or blockade within said blood vessel that occludes or controls blood flow through the vessel.

2. The medical, surgical, or operating kit for occluding or controlling blood flow of claim 1 wherein the sizes of said magnetic microparticles, magnetic nanoparticles, or magnetic colloids are in the size range of 0.01 μM to 2000μM, with (a) the maximum size of said magnetic microparticles, magnetic nanoparticles, or magnetic colloids being chosen such that they are smaller than the diameter of the venules, vessels, or capillaries, and (b) the maximum size of said magnetic microparticles, magnetic nanoparticles, or magnetic colloids being chosen such that they do not independently occlude blood flow without the applied external magnetic field.

3. The medical, surgical, or operating kit for occluding or controlling blood flow of claim 1 wherein said magnetic microparticles, magnetic nanoparticles, or magnetic colloids are comprised of any magnetizable materials including paramagnetic, superparamagnetic, ferrimagnetic, and ferromagnetic materials.

4. The medical, surgical, or operating kit for occluding or controlling blood flow of claim 1 wherein said magnetic microparticles, magnetic nanoparticles, or magnetic colloids are comprised of plain magnetic materials, surface-modified materials, surface-treated materials, coated microparticles, coated nanoparticles, microencapsulated microparticles, microencapsulated nanoparticles, microencapsulated microspheres, microencapsulated colloidal systems, microencapsulated liposomes and emulsions, or embedded systems comprised of magnetic ingredients.

5. The medical, surgical, or operating kit for occluding or controlling blood flow of claim 1 wherein said magnetic microparticles, magnetic nanoparticles, or magnetic colloids are comprised of or treated/encapsulated with emulsifiers, surfactants, lipids, polymers, copolymers, silicones, silanes, therapeutic drugs, pharmaceutical compounds, hemostatic agents, or other bioactive agents.

6. The medical, surgical, or operating kit for occluding or controlling blood flow of claim 1 wherein said external magnetic field source, when applied to humans or to animals, is either internal or external to the body, even though the said external magnetic field source is external to the particular blood vessel.

7. The medical, surgical, or operating kit for occluding or controlling blood flow of claim 1 wherein said external magnetic field source is comprised of:

(a) rare earth magnets including Neodymium Iron Boron magnets, bonded Neodymium Iron Boron magnets, and Samarium Cobalt magnets, or (b) ceramic magnets, or (c) ceramic ferrite magnets, or (d) Alnico magnets, or (e) electromagnets, or (f) superconducting magnets.

8. The medical, surgical, or operating kit for occluding or controlling blood flow of claim 1 wherein said magnetic microparticles, magnetic nanoparticles, or magnetic colloids are biodegradable or bioabsorbable.

9. The medical, surgical, or operating kit for occluding or controlling blood flow of claim 1 wherein said magnetic microparticles, magnetic nanoparticles, or magnetic colloids are suitable to be infused into a blood vessel.

10. The medical, surgical, or operating kit for occluding or controlling blood flow of claim 1 further includes a catheter or other devices for infusion, and wherein said magnetic microparticles, magnetic nanoparticles, or magnetic colloids are packaged in a suitable container for infusion into a blood vessel.

11. The medical, surgical, or operating kit for occluding or controlling blood flow of claim 1 utilizing non-invasive or minimally invasive procedures.

12. The medical, surgical, or operating kit for occluding or controlling blood flow of claim 1 having reversible effects upon removal of said external magnetic field source.

13. The medical, surgical, or operating kit for occluding or controlling blood flow of claim 1 having irreversible effects upon removal of said external magnetic field source.

14. The medical, surgical, or operating kit for occluding or controlling blood flow of claim 1 when used for any surgical application or medical application involving occlusion or control of blood flow in humans or in animals.

15. The medical, surgical, or operating kit for occluding or controlling blood flow of claim 1 when used for hemorrhage therapy in humans or in animals.

16. The medical, surgical, or operating kit for occluding or controlling blood flow of claim 1 when used for controlling or managing blood leaks.

17. A medical, surgical, or operating kit for occluding or controlling fluid flow comprised of:

(a) magnetic microparticles, magnetic nanoparticles, or magnetic colloids which can be administered in the form of a dispersion or suspension into a fluid vessel that flows though the vessel in the fluid flow, and (b) an external magnetic field source which is adapted to be placed or held at the desired site near or above the path of the fluid flow to form a plug or blockade within said fluid vessel that occludes or controls fluid flow though the vessel.

18. The medical, surgical, or operating kit for occluding or controlling fluid flow of claim 17 wherein the sizes of said magnetic microparticles, magnetic nanoparticles, or magnetic colloids are in the size range of 0.01 μM to 2000μM, with (a) the maximum size of said magnetic microparticles, magnetic nanoparticles, or magnetic colloids being chosen such that they are smaller than the diameter of the vessel of interest, and (b) the maximum size of said magnetic microparticles, magnetic nanoparticles, or magnetic colloids being chosen such that they do not independently occlude fluid flow without the applied external magnetic field.

19. The medical, surgical, or operating kit for occluding or controlling fluid flow of claim 17 wherein said magnetic microparticles, magnetic nanoparticles, or magnetic colloids are comprised of any magnetizable materials including paramagnetic, superparamagnetic, ferrimagnetic, and ferromagnetic materials.

20. The medical, surgical, or operating kit for occluding or controlling fluid flow of claim 17 wherein said magnetic microparticles, magnetic nanoparticles, or magnetic colloids. are comprised of plain magnetic materials, surface-modified materials, surface-treated materials, coated microparticles, coated nanoparticles, microencapsulated microparticles, microencapsulated nanoparticles, microencapsulated microspheres, microencapsulated colloidal systems, microencapsulated liposomes and emulsions, or embedded systems comprised of magnetic ingredients.

21. The medical, surgical, or operating kit for occluding or controlling fluid flow of claim 17 wherein said magnetic microparticles, magnetic nanoparticles, or magnetic colloids are comprised of or treated/encapsulated with emulsifiers, surfactants, lipids, polymers, copolymers, silicones, silanes, therapeutic drugs, pharmaceutical compounds, or other bioactive agents.

22. The medical, surgical, or operating kit for occluding or controlling fluid flow of claim 17 wherein said external magnetic field source is comprised of:
   (a) rare earth magnets including Neodymium Iron Boron magnets, bonded Neodymium Iron Boron magnets, and Samarium Cobalt magnets, or
   (b) ceramic magnets, or
   (c) ceramic ferrite magnets, or
   (d) Alnico magnets, or
   (e) electromagnets, or
   (f) superconducting magnets.

23. The medical, surgical, or operating kit for occluding or controlling fluid flow of claim 17 further includes a catheter or other devices for infusion, and wherein said magnetic microparticles, magnetic nanoparticles, or magnetic colloids are packaged in a suitable container for infusion into the vessel of interest.

24. The medical, surgical, or operating kit for occluding or controlling fluid flow of claim 17 having reversible effects upon removal of said external magnetic field source.

25. The medical, surgical, or operating kit for occluding or controlling fluid flow of claim 17 having irreversible effects upon removal of said external magnetic field source.

26. The medical, surgical, or operating kit for occluding or controlling fluid flow of claim 17 when used for any surgical application or medical application involving occlusion or control of fluid flow in humans or in animals.

27. The medical, surgical, or operating kit for occluding or controlling fluid flow of claim 17 when used for controlling or managing fluid leaks.

28. A device comprised of:
   (a) a dispersion or suspension of magnetic microparticles, magnetic nanoparticles, or magnetic colloids which can be made suitable in a suitable container to be administered into a blood vessel or fluid vessel that flows through the vessel in the bloodstream or fluid flow; and,
   (b) an external magnetic field source which can be adapted to be placed or held at a desired site near or above the path of the bloodstream or fluid flow to form a plug or blockade within said blood vessel or fluid vessel that occludes or controls blood flow or fluid flow through the vessel.

29. The device of claim 28 wherein the sizes of said magnetic microparticles, magnetic nanoparticles, or magnetic colloids are in the size range of $0.01\mu M$ to $2000\ \mu M$, with
   (a) the maximum size of said magnetic microparticles, magnetic nanoparticles, or magnetic colloids being chosen such that they are smaller than the diameter of the venules, vessels, or capillaries, and
   (b) the maximum size of said magnetic microparticles, magnetic nanoparticles, or magnetic colloids being chosen such that they do not independently occlude blood flow or fluid flow without the applied external magnetic field.

30. The device of claim 28 wherein said magnetic microparticles, magnetic nanoparticles, or magnetic colloids are comprised of any magnetizable materials including paramagnetic, superparamagnetic, ferrimagnetic, and ferromagnetic materials.

31. The device of claim 28 wherein said external magnetic field source is comprised of:
   (a) rare earth magnets including Neodymium Iron Boron magnets, bonded Neodymium Iron Boron magnets, and Samarium Cobalt magnets, or
   (b) ceramic magnets, or
   (c) ceramic ferrite magnets, or
   (d) Alnico magnets, or
   (e) electromagnets, or
   (f) superconducting magnets.

\* \* \* \* \*